(12) United States Patent
Wietelmann et al.

(10) Patent No.: US 9,260,456 B2
(45) Date of Patent: Feb. 16, 2016

(54) PROCESS FOR PREPARING METAL DIFLUOROCHELATOBORATES AND USE AS BATTERY ELECTROLYTES OR ADDITIVES IN ELECTROCHEMICAL CELLS

(71) Applicant: Rockwood Lithium GmbH, Franfurt a. M. (DE)

(72) Inventors: Ulrich Wietelmann, Friedrichsdorf (DE); Peter Rittmeyer, Suzbach/Taunus (DE); Ute Emmel, Frankfurt am Main (DE)

(73) Assignee: Rockwood Lithium GmbH (DE)

( * ) Notice: Subject to any disclaimer, the term of this patent is extended or adjusted under 35 U.S.C. 154(b) by 0 days.

(21) Appl. No.: 14/357,919

(22) PCT Filed: Nov. 14, 2012

(86) PCT No.: PCT/EP2012/072603
§ 371 (c)(1),
(2) Date: May 13, 2014

(87) PCT Pub. No.: WO2013/072359
PCT Pub. Date: May 23, 2013

(65) Prior Publication Data
US 2014/0288331 A1 Sep. 25, 2014

(30) Foreign Application Priority Data
Nov. 14, 2011 (DE) .......................... 10 2011 086 306

(51) Int. Cl.
C07F 5/02 (2006.01)
C07F 5/04 (2006.01)
H01M 10/0567 (2010.01)

(52) U.S. Cl.
CPC ............... *C07F 5/025* (2013.01); *C07F 5/022* (2013.01); *C07F 5/04* (2013.01); *H01M 10/0567* (2013.01)

(58) Field of Classification Search
CPC ............ C07C 5/025; C07C 5/04; C07C 5/022
USPC .......................................................... 568/6
See application file for complete search history.

(56) References Cited

U.S. PATENT DOCUMENTS

| | | |
|---|---|---|
| 6,783,896 B2 | 8/2004 | Tsujioka et al. |
| 6,849,752 B2 | 2/2005 | Tsujioka et al. |
| 7,709,663 B2 | 5/2010 | Wietelmann et al. |
| 8,168,806 B2 | 5/2012 | Wietelmann et al. |
| 2004/0063986 A1 | 4/2004 | Wietelmann et al. |
| 2012/0082900 A1 | 4/2012 | Wietelmann et al. |

FOREIGN PATENT DOCUMENTS

| | | |
|---|---|---|
| CN | 101643481 B * | 8/2011 |
| EP | 1 195 834 A2 | 4/2002 |
| EP | 1 308 449 A2 | 5/2003 |
| WO | 02/068432 A1 | 9/2002 |
| WO | 2010/094467 A1 | 8/2010 |

OTHER PUBLICATIONS

Chen, et al. "Lithium Difluoro(oxalato)borate as Salt for Lithium-Ion Batteries", Electrochemical and Solid-State Letters, 10 (3), (2007), pp. A45-A47.
Schreiner, et al. "Chloride-Free Method to Synthesise New Ionic Liquids with Mixed Borate Anions", Chem. Eur. J., 15 (2009), pp. 2270-2272.
Zhang, Sheng Shui "An unique lithium salt for the improved electrolyte of Li-ion battery", Electrochemistry Communications, 8 (2006), pp. 1423-1428.
Zhou, et al. "Investigation of the Disproportionation Reactions and Equilibrium of Lithium Difluoro(Oxalato) Borate (LiDFOB)", Electrochemical and Solid-State Letters, 14 (11), (2011), pp. A161-A164.
Xue, et al. "A new lithium salt with dihydroxybenzene and lithium tetrafluoroborate for lithium battery electrolytes", J. of Power Sources, 196 (2011), pp. 8710-8713.

* cited by examiner

*Primary Examiner* — Yong Chu

(57) ABSTRACT

The invention relates to a process for preparing metal difluorochelatoborates, in which a metal bis(chelato)borate of the formula $M[BL_2]$ is reacted with boron trifluoride and a metal fluoride (MF) and/or a metal salt of the chelating ligand ($M_2L$) where M+ is a monovalent cation selected from the group consisting of lithium, sodium, potassium and ammonium $NR_4^+$, where R=H, alkyl (C1 to C8) and L is a chelating agent having two terminal oxygen atoms and having the general formula (II), where: when m=1 and $Y^1$ and $Y^2$ together with $C^1$ form a carbonyl group, n=0 or 1 and o=0 or 1 and $R^1$ and $R^2$ are each, independently of one another, H or alkyl having from one to eight carbon atoms (C1-C8) and $Y^3$, $Y^4$ are each, independently of one another, $OR^3$ ($R^3$=C1-C8-alkyl), then n or o≠1: p=0 or 1 and when n and o=0, p=1; or $Y^1$, $Y^2$, $Y^3$, $Y^4$ are each, independently of one another, $OR^3$ ($R^3$=C1-C8-alkyl), m=1, n=0 or 1, o=1 and p=0; or $C^2$ and $C^3$ are members of a 5- or 6-membered aromatic or heteroaromatic ring (with N, O or S as heteroelement) which can optionally be substituted by alkyl, alkoxy, carboxy or nitrile, where $R^1$, $R^2$, $Y^3$ and $Y^4$ are absent, m=0 or in the case of 1, $Y^1$ and $Y^2$ together with $C^1$ form a carbonyl group and p is 0 or 1, in an organic, aprotic solvent.

(II)

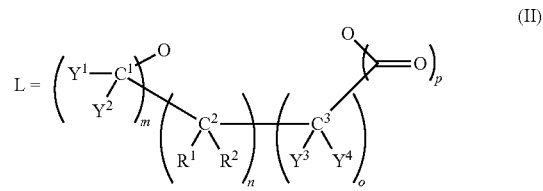

16 Claims, No Drawings

PROCESS FOR PREPARING METAL DIFLUOROCHELATOBORATES AND USE AS BATTERY ELECTROLYTES OR ADDITIVES IN ELECTROCHEMICAL CELLS

This application is a §371 of International Application No. PCT/EP2012/072603 filed Nov. 14, 2012, and claims priority from German Patent Application No. 10 2011 086 306.0 filed Nov. 14, 2011.

The invention relates to a process for preparing metal difluorochelatoborates, and their use as battery electrolytes or additives in electrochemical cells.

Mobile electronic devices require increasingly more powerful rechargeable batteries for independently supplying power. In addition to nickel/cadmium and nickel/metal hydride batteries, lithium batteries in particular, which have much higher energy densities than the first-mentioned systems, are suitable for this purpose. In the future, large-scale lithium batteries will also be used, for example, for stationary applications (power back-up) and in the automotive sector for traction purposes (hybrid drives or solely electric drives). Great importance is attached to reliability, in particular for the latter-mentioned applications.

The current generation of lithium-ion batteries presently in use utilizes as an electrolyte liquid, gel, or polymer electrolytes containing $LiPF_6$ as the conductive salt. This salt starts to decompose when the temperature exceeds approximately 70° C., and forms the highly reactive Lewis acid $PF_5$ according to the formula $$LiPF_6 \rightarrow LiF + PF_5 \qquad (1).$$

The acid attacks the organic components of the electrolytes (alkyl carbonates, for example) used according to the prior art. This reaction is exothermic, and may result in "run-away" self-heating. Thus, at the minimum the functionality of the electrochemical cell is impaired, or the cell may be completely destroyed, with hazardous repercussions.

As an alternative electrolyte, solutions of lithium salts containing fluorochelatoborate anion, such as lithiumdifluorooxalatoborate (LiDFOB) (U.S. Pat. No. 6,849,752 Z. Chen, J. Liu, K. Amine, Electrochem. Solid State Lett. 10 (2007) A45-47) or lithium difluoro(1,2-benzenediolato(2-)-O,O'-borate (X. Zhao-Ming, J. Power Sources 196 (2011) 8710), among others, have been proposed.

The following discussions focus on the conductive salt LiDFOB. However, they also analogously apply for variations of this structure according to general formula I

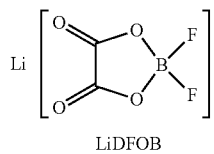

LiDFOB

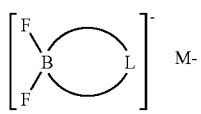  M-

General formula I where $M^+$ is a monovalent cation selected from the group lithium, sodium, potassium, or ammonium $NR_4^+$, and R=H or alkyl (C1 to C8, acyclic or cyclic), L is a chelating agent, having two terminal oxygen atoms, with the general formula

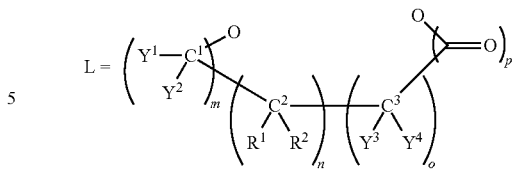

where the following apply:

when m=1 and $Y^1$ and $Y^2$ together with $C^1$ stand for a carbonyl group, n=0 or 1 and o=0 or 1, and $R^1$ and $R^2$ are each independently H or alkyl containing one to eight carbon atoms (C1-C8), and $Y^3$, $Y^4$ are each independently $OR^3$ ($R^3$=C1-C8 alkyl), and when n or o≠1, p=0 or 1, and when n and o=0, p=1;

or $Y^1$, $Y^2$, $Y^3$, $Y^4$ are each independently $OR^3$ ($R^3$=C1-C8 alkyl), m=1, n=0 or 1, o=1, and p=0;

or $C^2$ and $C^3$ are members of a 5- or 6-membered aromatic or heteroaromatic ring (with N, O, or S as heteroelement) which may optionally be substituted with alkyl, alkoxy, carboxy, or nitrile, where $R^1$, $R^2$, $Y^3$, and $Y^4$ are absent when m=0, or in the case of [m=] 1, $Y^1$ and $Y^2$ together with $C^1$ stand for a carbonyl group, and p is 0 or 1.

The conductive salt LiDFOB ($M^+$=Li and L=$C_2O_4^{2-}$) may be prepared in various ways.

In the reaction of lithium tetrafluoroborate ($LiBF_4$) with 2 equivalents lithium hexafluoroisopropanolate in acetonitrile, initially lithium fluoride (LiF) is eliminated (EP 1195834). The alkoxy ligands of the intermediate product, which are only relatively weakly bonded, are replaced by the better chelate donor, oxalate, in a second step:

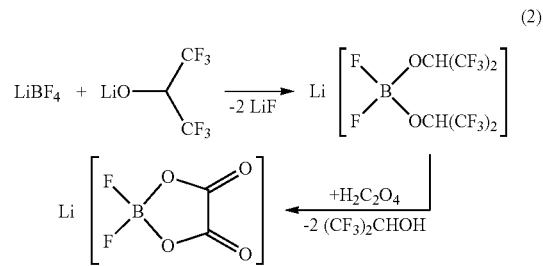

(2)

In this method it is disadvantageous that LiF remains in the product, the ligand 1,1,1,3,3,3-hexafluoroisopropanol is costly, and the process is complicated due to having two steps.

In another production method, lithium tetrafluoroborate is reacted with anhydrous oxalic acid and $SiCl_4$ as auxiliary reagent (EP 1308449):

$$2LiBF_4 + 2H_2Ox + SiCl_4 \rightarrow Li[F_2BOx] + 4HCl + SiF_4 \qquad (3)$$

A disadvantage of this synthesis is the formation of the acidic, toxic co-products $SiF_4$ and HCl. In addition, traces of chloride remain in the product. It is known that chloride is corrosive to aluminum, so that a conductive salt which is thus contaminated with chloride corrodes the cathode current collector, generally an aluminum foil, used in Li-ion batteries.

It is also known that in heat aging of equimolar mixtures of $LiBF_4$ and LiBOB in ethylene carbonate/ethylmethyl carbonate (EC/EMC), LiDFOB forms in a very slow reaction (B. Lucht, Electrochem. Solid-State Lett. 14 (11) A161-A164 (2011)). Thus, when the mixed salt LiDFOB is stored at 100° C., an approximately 80% yield is obtained within 10 weeks.

The disadvantages of this method are that the reaction is much too slow for commercial use, and the raw material LiBF$_4$ is costly.

In another method, boron trifluoride, usually in the form of an ether addition product, is reacted with lithium oxalate (S. S. Zhang, Electrochem. Commun. 8 (2006) 1423-1428):

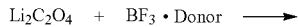

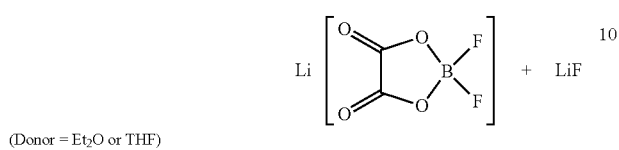

(Donor = Et$_2$O or THF)

A disadvantage of this method is that the target product LiDFOB is formed in a yield of only 50%, and LiBF$_4$ forms to the same extent. Namely, the by-product LiF which results according to Equation (4) reacts immediately with boron trifluoride to form LiBF$_4$, so that overall, the following reaction equation applies:

$$Li_2C_2O_4 + 2BF_3 \rightarrow Li[F_2BC_2O_4] + LiBF_4 \tag{4a}$$

Lastly, LiDFOB may be prepared from lithium tetrafluoroborate and bis(trimethylsilyl)oxalate in acetonitrile solution (C. Schreiner, M. Amereller, H. Gores, Chem. Eur. J. 13 (2009) 2270-2272):

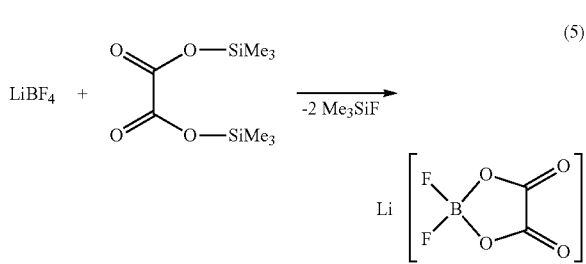

Disadvantages of this method are the high costs, the unavailability of the silyl ester, and occurrence of the by-product trimethylsilyl fluoride.

The object of the invention is to provide a process which, starting from commercially available, easily handled raw materials, forms metal difluorochelatoborates, in particular LiDFOB, in a simple one-step reaction.

The object is achieved by reacting a metal bis(chelato) borate of formula M[BL$_2$] with boron trifluoride and a metal fluoride (MF) and/or a metal salt of the chelate ligand (M$_2$L) in an organic aprotic solvent, where M$^+$ is a monovalent cation selected from the group lithium, sodium, potassium, or ammonium NR$_4^+$, where R=H or alkyl (C1 to C8, acyclic or cyclic), and L is a chelating agent having two terminal oxygen atoms having the general formula

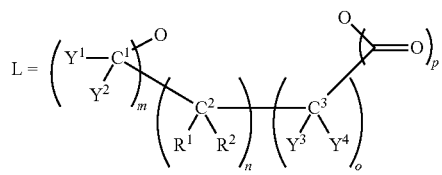

where the following apply:
when m=1 and Y$^1$ and Y$^2$ together with C$^1$ stand for a carbonyl group, n=0 or 1 and o=0 or 1, and R$^1$ and R$^2$ are independently H or alkyl containing one to eight carbon atoms (C1-C8), and Y$^3$, Y$^4$ are each independently OR$^3$ (R$^3$=C1-C8 alkyl), and when n or o≠1, p=0 or 1, and when n and o=0, p=1;

or

Y$^1$, Y$^2$, Y$^3$, Y$^4$ are each independently OR$^3$ (R$^3$=C1-C8 alkyl), m=1, n=0 or 1, o=1, and p=0; or C$^2$ and C$^3$ are members of a 5- or 6-membered aromatic or heteroaromatic ring (with N, O, or S as heteroelement) which may optionally be substituted with alkyl, alkoxy, carboxy, or nitrile, where R$^1$, R$^2$, Y$^3$ and Y$^4$ are absent when m=0, or in the case of [m=] 1, Y$^1$ and Y$^2$ together with C$^1$ stand for a carbonyl group and p is 0 or 1.

The reactions may be described by the following general equations:

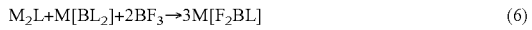

For the case of preparation of the particularly preferred conductive salt LiDFOB, lithium bis(oxalato)borate (LiBOB) is reacted with lithium fluoride or lithium oxalate and boron trifluoride:

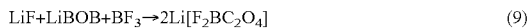

Similarly, the likewise particularly preferred conductive salt lithium difluoromalonatoborate (LiDFMB) is prepared from lithium-bis(malonato)borate and BF$_3$ as well as LiF or lithium malonate (Li$_2$C$_3$H$_2$O$_4$). Further preferred products are the following: lithium difluorolactatoborate, lithium difluoroglycolatoborate, lithium difluorosalicylatoborate, lithium difluorocatecholatoborate, and the corresponding sodium salts. Aprotic organic solvents, preferably ethers, esters, nitriles, lactones, or carbonates, are used either in pure form or in any given mixture. In addition, hydrocarbons (aromatics or saturated compounds) may be used in mixtures with the above-mentioned functionalized solvents.

The use of solvents which are suitable for use in lithium batteries is very particularly preferred. Such solvents include the following: carboxylic acid esters (dimethyl carbonate, diethyl carbonate, ethylmethyl carbonate, propylene carbonate, ethylene carbonate), cyclic ethers such as tetrahydropyran or tetrahydrofuran, polyethers such as 1,2-dimethoxyethane or diethylene glycol dimethyl ether, as well as nitriles such as acetonitrile, adiponitrile, malodinitrile, and glutaronitrile, and lactones such as γ-butyrolactone.

The reaction is carried out at temperatures between 0 and 250° C., preferably between 20 and 150° C., particularly preferably between 30 and 130° C.

The sparingly soluble raw materials, i.e., the metal fluorides and/or metal chelate salts, are used in pulverized form, preferably ground. The average particle size is <100 μm, particularly preferably <50 μm.

All raw materials, in particular the metal salts and the solvents, are used in anhydrous form; i.e., the water content of the raw materials is <1000 ppm, preferably <300 ppm.

In one particularly preferred embodiment, a reaction acceleration catalyst is used. Lewis acids or substances which release or are able to release Lewis acids in the reaction mixture are used as catalyst. Preferred catalysts are compounds of elements Groups 2 through 15 of the periodic table, particularly preferably molecular halides, perfluoroalkyls, perfluoroaryls, and oxo compounds of boron, aluminum, and phosphorus. Examples include the following: aluminum alcoholates (Al(OR)$_3$), boric acid esters (B(OR)$_3$), phosphorus oxides, and phosphorus halides. Very particularly preferred are superacid boron compounds such as B(C$_6$F$_5$)$_3$ (BARF), C$_6$F$_5$BO$_2$C$_6$F$_4$, and boric acid esters of trivalent oxygen-based chelate ligands such as the following:

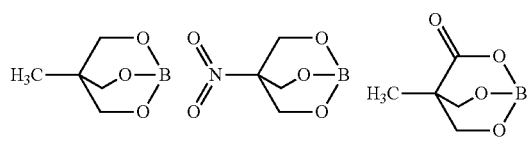

In addition, very particularly preferred is the catalytic use of LiPF$_6$, which under the above-mentioned reaction conditions is in equilibrium with the strong Lewis acid PF$_5$ (Equation 1). The mentioned catalysts are used in quantities of 20 mol-% maximum, preferably up to 10 mol-% and particularly preferably up to 5 mol-%, based on the boron trifluoride used.

The process according to the invention is described in general terms below. The metal salts are placed in the anhydrous solvent. With stirring, boron trifluoride is then either introduced or condensed in the gaseous state, or added in the form of standard solvate complexes such as BF$_3$×diethyl ether, BF$_3$×THF, or BF$_3$×acetonitrile. The use of gaseous BF$_3$ or a solution prepared beforehand with BF$_3$ gas in the desired solvent (for example, a carbonate such as dimethyl carbonate or propylene carbonate) is particularly preferred. The introduction of a solvent, such as diethyl ether, which is uncommon or even detrimental in battery electrolytes, is thus avoided. BF$_3$ is added in a temperature range between 0° C. and 150° C., preferably between 10° C. and 100° C. After the BF$_3$ has been added, stirring is performed until the reaction is complete. The progress of the reaction may be conveniently monitored by $^{11}$B NMR measurements, for example.

The process according to the invention may also deviate slightly from the theoretical stoichiometry (Equations 6 through 9). The stoichiometries are preferably selected which result in complete consumption of the raw material BF$_3$, which has a detrimental effect in the battery. For this purpose, the metal salts MF and/or M$_2$L are used in excess. The mentioned metal salts are preferably used in an excess of 0.1 to 100% by weight, particularly preferably in an excess of 1 to 20% by weight.

After the reaction is complete, the reaction solution is clarified by membrane filtration, for example. The reaction solution is then directly usable as such as a battery electrolyte or additive, if no solvents which are detrimental to the battery performance have been used. In the event that detrimental solvents are contained, the synthesized metal difluorochelatoborate according to the invention is obtained in pure form by means of a concentration or crystallization process.

The invention is explained with reference to the following seven examples.

EXAMPLE 1

Preparation of LiDFOB from LiBOB, Lithium Oxalate, and BF$_3$ in Dimethyl Carbonate (DMC)

37.5 g LiBOB and 19.8 g Li$_2$C$_2$O$_4$ in 229 g anhydrous DMC were placed in a 0.5-L double shell reactor equipped with a reflux cooler and dropping funnel, and heated to an internal temperature of 70° C. 55.0 g boron trifluoride etherate was then metered in over a period of one hour. The jacket temperature was set so that the reaction mixture was boiling lightly the entire time. After metering was complete, refluxing was continued with occasional withdrawal of samples.

The samples were checked for progress of the reaction by $^{11}$B NMR:

| Time of sampling | −1.1 ppm* LiBF$_4$ | 0 ppm* BF$_3$ | 3.1 ppm* LiDFOB | 7.6 ppm* LiBOB |
|---|---|---|---|---|
| End of metering | 41.5 | 4.7 | 42.9 | 10.8 |
| 2 h after the reaction | 43.0 | 3.0 | 45.9 | 8.2 |
| 7.5 h after the reaction | 37.8 | 3.9 | 47.6 | 10.7 |
| 9 h after the reaction | 36.9 | 2.9 | 48.4 | 11.8 |
| 11.5 h after the reaction | 37.7 | 2.6 | 55.3 | 4.5 |
| 18.5 h after the reaction | 17.6 | 2.2 | 66.7 | 13.6 |
| 26 h after the reaction | 9.2 | 1.9 | 78.9 | 8.9 |
| 30 h after the reaction | 8.8 | 2.1 | 81.4 | 7.7 |

*Listed values represent the chemical shift of the particular product in the $^{11}$B NMR spectrum After a 30-hour reaction time, >80% of theoretical LiDFOB had formed, and the composition did not change significantly with continued stirring. Thus, a thermodynamic equilibrium mixture was formed. The reaction mixture was filtered, and was used in this form (clear solution) as an electrolyte for lithium batteries.

EXAMPLE 2

Preparation of LiDFOB from LiBOB, Lithium Oxalate, and BF$_3$ in Dimethyl Carbonate (DMC), 5 mol-% LiPF$_6$ Catalyst 1.50 g LiBOB and 0.91 g lithium oxalate were dissolved or suspended in 9.16 g DMC in an inerted GC septum glass equipped with a magnetic stirrer, and 0.59 g of a 10% LiPF$_6$ solution in DMC was added. 2.20 g boron trifluoride etherate was injected into the stirred suspension, which was then heated to 70° C. Samples were withdrawn at specified time intervals and checked for progress of the reaction by $^{11}$B NMR:

| Time of sampling | −1.1 ppm* LiBF$_4$ | 0 ppm* BF$_3$ | 3.1 ppm* LiDFOB | 7.6 ppm* LiBOB |
|---|---|---|---|---|
| 1 h, 70° C. | 41.5 | 0.5 | 46 | 8 |
| 5 h, 70° C. | 16 | 1.1 | 72 | 11 |
| 12 h, 70° C. | 14 | 1.0 | 79 | 6 |

*Listed values represent the chemical shift of the particular product in the $^{11}$B NMR spectrum

EXAMPLE 3

Preparation of LiDFOB from LiBOB, Lithium Oxalate, and BF$_3$ in Propylene Carbonate (PC), with and without 5 Mol-% LiPF$_6$ Catalyst 1.50 g LiBOB and 0.79 g lithium oxalate were dissolved or suspended in 9.2 g PC in each of two inerted GC septum glasses equipped with a magnetic stirrer. 0.59 g of a 10% solution of LiPF$_6$ in PC was injected into one of the glasses. 2.20 g boron trifluoride etherate was injected into each of the stirred suspensions, which were then heated to 70° C. Samples were withdrawn at specified time intervals and checked for progress of the reaction by $^{11}$B NMR:

| | LiBF4 | | LiDFOB | | LiBOB | |
|---|---|---|---|---|---|---|
| Reaction time 70° C. (h) | Without catalyst | With catalyst | Without catalyst | With catalyst | Without catalyst | With catalyst |
| 1 h | 32 | 22 | 40 | 62 | 28 | 16 |
| 2 h | 31 | 18 | 41 | 71 | 27 | 11 |
| 9 h | 28 | 10 | 54 | 83 | 18 | 6 |

EXAMPLE 4

Preparation of LiDFOB from LiBOB, Lithium Fluoride and $BF_3$ in Propylene Carbonate (PC) with 5 mol-% $LiPF_6$ Catalyst 1.50 g LiBOB and 0.23 g ground lithium fluoride were dissolved or suspended in 6.8 g PC in an inerted GC septum glass equipped with a magnetic stirrer, and 0.59 g of a 10% $LiPF_6$ solution in PC was added. 1.10 g boron trifluoride etherate was injected into the stirred suspension, which was then heated to 70° C. Samples were withdrawn at specified time intervals and checked for progress of the reaction by $^{11}B$ NMR:

| Time of sampling | −1.1 ppm* LiBF4 | 0 ppm* BF3 | 3.1 ppm* LiDFOB | 7.6 ppm* LiBOB |
|---|---|---|---|---|
| 1 h, 70° C. | 19 | 0.4 | 68 | 13 |
| 2 h, 70° C. | 15 | 0.5 | 74 | 11 |
| 9 h, 70° C. | 9 | 1 | 86 | 4 |

*Listed values represent the chemical shift of the particular product in the $^{11}B$ NMR spectrum

EXAMPLE 5

Preparation of LiDFOB from LiBOB, Lithium Fluoride, and $BF_3$ in Tetrahydropyran (THP), without Catalyst 1.50 g LiBOB and 0.25 g ground lithium fluoride were dissolved or suspended in 8.5 g THP in an inerted GC septum glass equipped with a magnetic stirrer. 1.10 g boron trifluoride etherate was injected into the stirred suspension, which was then heated to 70° C. Samples were withdrawn at specified time intervals and checked for progress of the reaction by $^{11}B$ NMR:

| Time of sampling | −1.1 ppm* LiBF4 | 0 ppm* BF3 | 3.1 ppm* LiDFOB | 7.6 ppm* LiBOB |
|---|---|---|---|---|
| 15 min, 70° C. | 28 | 0 | 47 | 25 |
| 2 h, 70° C. | 16 | 0.5 | 79 | 4 |

*Listed values represent the chemical shift of the particular product in the $^{11}B$ NMR spectrum

EXAMPLE 6

Preparation of LiDFMB from Lithium-bis(malonato)borate (LiBMB), Lithium Fluoride, and $BF_3$ in Propylene Carbonate (PC), without Catalyst 1.78 g LiBMB and 0.21 g lithium fluoride were suspended in 11 g PC in an inerted GC septum glass equipped with a magnetic stirrer. 1.14 g boron trifluoride etherate was injected into the stirred suspension, which was then stirred at 100° C. Samples were withdrawn at specified time intervals and checked for progress of the reaction by $^{11}B$ NMR:

| Time of sampling | −1.2 ppm* LiBF4 | 0 ppm* BF3 | 1.4 ppm* LiDFMB | 3.6 ppm* LiBMB |
|---|---|---|---|---|
| 30 min, 100° C. | 29 | 4 | 54 | 11 |
| 2.5 h, 100° C. | 29 | 4 | 61 | 5 |
| 7 h, 100° C. | 24 | 3 | 70 | 3 |

*Listed values represent the chemical shift of the particular product in the $^{11}B$ NMR spectrum

EXAMPLE 7

Preparation of LiDFMB from Lithium-bis(malonato)borate (LiBMB), Lithium Fluoride, and $BF_3$ in Dimethylsulfoxide (DMSO), without Catalyst 1.78 g LiBMB and 0.21 g lithium fluoride were dissolved or suspended in 10.5 g DMSO in an inerted GC septum glass equipped with a magnetic stirrer. 1.14 g boron trifluoride etherate was injected into the stirred suspension, which was then stirred at 100° C. An almost clear reaction solution formed after a short time. Samples were withdrawn at specified time intervals and checked for progress of the reaction by $^{11}B$ NMR:

| Time of sampling | −1.2 ppm* LiBF4 | 0 ppm* BF3 | 1.4 ppm* LiDFMB | 3.6 ppm* LiBMB |
|---|---|---|---|---|
| 30 min, 100° C. | 19 | 2 | 45 | 34 |
| 2.5 h, 100° 0 | 11 | 0.9 | 67 | 20 |
| 7 h, 100° C. | 6 | approx. 0 | 83 | 11 |

*Listed values represent the chemical shift of the particular product in the $^{11}B$ NMR spectrum

The invention claimed is:

1. A process for preparing a metal difluoroborate of formula

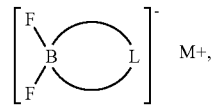

wherein $M^+$ is a monovalent cation selected from the group consisting of lithium, sodium, and potassium; and
L is a chelating agent selected from the group consisting of lactate, glycolate, salicylate, catecholate, oxalate and malonate;
comprising the steps of reacting a metal bis(chelato)borate of formula $M[BL_2]$ with boron trifluoride and a metal fluoride (MF) or a metal salt of the chelate ligand ($M_2L$) in an organic aprotic solvent.

2. A process according to claim 1, wherein $M^+$ is lithium and wherein L is oxalate or malonate, and wherein the product is lithium difluorooxalatoborate.

3. A process according to claim 1, wherein the solvent comprises at least one member selected from the group consisting of an ether, an ester, a nitrile, a lactone and an alkyl carbonate.

4. A process according to claim 1, wherein the solvent comprises at least one member selected from the group consisting of a carboxylic acid ester, a cyclic ether, a polyether, a nitrile and a lactone.

5. A process according to claim 1, wherein the reaction is carried out at temperatures of 0 to 250° C.

6. A process according to claim 1, wherein at least one of the metal fluorides and metal chelate salts are in pulverized form.

7. A process according to claim 1, wherein the metal salts of at least one of MF and $M_2L$ are used in excess.

8. A process according to claim 1, wherein the metal salts MF and/or $M_2L$ are used in an excess of 0.1 to 100% by weight.

9. A process according to claim 1, wherein a reaction acceleration catalyst is used during the process.

10. A process according to claim 9, wherein the catalyst contains or is composed of a Lewis acid or a substance which releases a Lewis acid in the reaction mixture.

11. A process according to claim 9, where the catalyst is selected from the group consisting of an element from Groups 2 through 15 of the periodic table, a perfluoroalkyl, a perfluoroaryl, an oxo compound of boron, an oxo compound of aluminum and an oxo compound of phosphorus.

12. A process according to claim 9, wherein the catalyst is $LiPF_6$.

13. A process according to claim 9, wherein the catalyst is used in quantities of 20 mol-% maximum based on the boron trifluoride used.

14. An electrochemical cell comprising the metal difluoroboarate prepared according to the process of claim 1.

15. A process according to claim 1, wherein the solvent is selected from the group consisting of dimethyl carbonate, diethyl carbonate, ethylmethyl carbonate, propylene carbonate, ethylene carbonate, tetrahydropyran, tetrahydrofuran, 1,2-dimethoxyethane, diethylene glycol dimethyl ether, acetonitrile, adiponitrile, malodinitrile, glutaronitrile and γ-butyrolactone.

16. A process according to claim 9, wherein the catalyst is selected from the group consisting of an aluminum alcoholate, a boric acid ester, a phosphorus oxide and a phosphorus halide.

* * * * *